US011617531B2

(12) United States Patent
Chen (10) Patent No.: US 11,617,531 B2
(45) Date of Patent: Apr. 4, 2023

(54) CIRCUIT APPLIED TO BIOPOTENTIAL ACQUISITION SYSTEM

(71) Applicant: MEDIATEK INC., Hsin-Chu (TW)

(72) Inventor: Chih-Hsin Chen, Hsin-Chu (TW)

(73) Assignee: MEDIATEK INC., Hsin-Chu (TW)

( * ) Notice: Subject to any disclaimer, the term of this patent is extended or adjusted under 35 U.S.C. 154(b) by 294 days.

(21) Appl. No.: 16/681,737

(22) Filed: Nov. 12, 2019

(65) Prior Publication Data

US 2020/0163574 A1 May 28, 2020

Related U.S. Application Data

(60) Provisional application No. 62/770,868, filed on Nov. 23, 2018.

(51) Int. Cl.
*A61B 5/301* (2021.01)
*H03F 3/45* (2006.01)
*A61B 5/25* (2021.01)

(52) U.S. Cl.
CPC .............. *A61B 5/301* (2021.01); *A61B 5/25* (2021.01); *H03F 3/45941* (2013.01); *H03F 2200/261* (2013.01)

(58) Field of Classification Search
CPC ....... A61B 5/301; A61B 5/25; H03F 3/45941; H03F 2200/261
USPC ..................................................... 600/509
See application file for complete search history.

(56) References Cited

U.S. PATENT DOCUMENTS

| 5,293,169 A * | 3/1994 | Baumgartner | H03M 3/398 341/172 |
| 6,208,888 B1 * | 3/2001 | Yonce | H03F 3/45475 600/509 |
| 6,496,721 B1 * | 12/2002 | Yonce | A61B 5/30 600/509 |
| 7,391,257 B1 * | 6/2008 | Denison | A61B 5/7217 330/10 |
| 8,817,834 B2 * | 8/2014 | Wang | H04L 27/361 600/509 |

(Continued)

FOREIGN PATENT DOCUMENTS

| CN | 101821852 A | 9/2010 |
| CN | 102403967 A | 4/2012 |

(Continued)

OTHER PUBLICATIONS

Texas Instruments: "TL071 TL07xx Low Noise JFET input Operational Amplifiers", Jul. 26, 2017 (Jul. 26, 2017), XP055654940, URL: http://www.ti.com/lit/gpn/tl072 (Year: 2017).*

(Continued)

*Primary Examiner* — Carl H Layno
*Assistant Examiner* — Michael J Lau
(74) *Attorney, Agent, or Firm* — Winston Hsu (57) ABSTRACT

The present invention provides a circuit applied to a biopotential acquisition system, wherein the circuit includes an active current source and an amplifier. In the operations of the circuit, the active current source is configured to provide a current to two input terminals of the circuit, wherein the two input terminals of the circuit are coupled to two input electrodes of the biopotential acquisition system; and the amplifier is configured to receive input signals from the two input terminals to generate an output signal.

18 Claims, 9 Drawing Sheets

(56) References Cited

U.S. PATENT DOCUMENTS

| | | | |
|---|---|---|---|
| 9,667,233 B2* | 5/2017 | Peschke | H03K 5/003 |
| 11,234,652 B2* | 2/2022 | Felix | A61B 5/25 |
| 2003/0102909 A1* | 6/2003 | Motz | G01R 33/075 |
| | | | 330/9 |
| 2004/0210148 A1 | 10/2004 | Van Ess | |
| 2010/0289568 A1* | 11/2010 | Eschauzier | H03F 3/45475 |
| | | | 330/9 |
| 2010/0327887 A1* | 12/2010 | Denison | H03F 3/45744 |
| | | | 324/123 R |
| 2012/0089036 A1 | 4/2012 | Felix | |
| 2012/0293258 A1* | 11/2012 | Fant | H03F 3/087 |
| | | | 330/252 |
| 2013/0116577 A1* | 5/2013 | Yazicioglu | H01L 27/0811 |
| | | | 600/483 |
| 2014/0266440 A1* | 9/2014 | Itagaki | H03F 1/26 |
| | | | 330/254 |
| 2015/0005585 A1* | 1/2015 | Xu | A61B 5/291 |
| | | | 600/300 |
| 2015/0119747 A1* | 4/2015 | Torfs | A61B 5/053 |
| | | | 600/547 |
| 2015/0173683 A1* | 6/2015 | Kim | A61B 5/7214 |
| | | | 600/509 |
| 2017/0153279 A1* | 6/2017 | Chung | G01R 19/0007 |
| 2017/0188864 A1* | 7/2017 | Drury | A61B 5/02427 |
| 2017/0207761 A1* | 7/2017 | Raman | H03F 3/005 |
| 2018/0055409 A1* | 3/2018 | Xu | H03F 3/45 |
| 2018/0115320 A1* | 4/2018 | Sharma | H03M 3/422 |

FOREIGN PATENT DOCUMENTS

| | | |
|---|---|---|
| CN | 103248393 A | 8/2013 |
| CN | 105476628 A | 4/2016 |
| CN | 106419894 A | 2/2017 |
| DE | 10 2014 214 994 A1 | 2/2016 |
| KR | 10-1693809 B1 | 1/2017 |
| TW | M496455 U | 3/2015 |
| TW | 201717846 A | 6/2017 |

OTHER PUBLICATIONS

Dobrev D etal: "Two Electrode Biopotential Amplifier With Current Driven Inputs", Medical and Biological Engineering and Computing, Springer, Heildelberg, DE, vol. 40, No. 1, Jan. 1, 2002 (Jan. 1, 2002), pp. 122-127, XP001178769, ISSN: 0140-0118, DOI: 10.1007BF02347705 (Year: 2002).*

In-Duk Hwang etal: "Direct Interference Canceling for Two Electrode Biopotential Amplifier", IEEE Transactions on Biomedical Engineering, IEEE Service Center Piscataway,NJ, USA, vol. 55, No. 11, Nov. 1, 2008 (Nov. 1, 2008), pp. 2620-2627, XP011342764, ISSN: 0018-9294, DOI: 10.1109/TBME.2008.92108 (Year: 2008).*

D. Dobrev et al., Two-electrode biopotential amplifier with current-driven inputs, Medical & Biological Engineering & Computing 2002, vol. 40, pp. 122-127, XP001178769, 2002.

Texas Instruments, TL07xx Low-Noise JFET-Input Operational Amplifiers, Jul. 2017, XP055654940.

Enrique M. Spinelli, "Two-Electrode Biopotential Measurements: Power Line Interference Analysis", IEEE Transactions on Biomedical Engineering, vol. 52, No. 8, Aug. 2005, Aug. 2005.

In-Duk Hwang, "Direct Interference Canceling for Two-Electrode Biopotential Amplifier", IEEE Transactions on Biomedical Engineering, vol. 55, No. 11, Nov. 2008, Nov. 2008.

Long Yan, "A Low-Power Portable ECG Touch Sensor with Two Dry Metal Contact Electrodes", Journal of Semiconductor Technology and Science, vol. 10, No. 4, Dec. 2010, Dec. 2010.

Carlos D. M. Pereira, "Development of a two-electrode ECG acquisition system with dynamic interference rejection", Feb. 2011.

Analog devices, "50 uA, 2 mm x 1.7 mm WLCSP, Low Noise, Heart Rate Monitor for Wearable Products", 2016.

Texas Instruments, "ADS129x Low-Power, 8-Channel, 24-Bit Analog Front-End for Biopotential Measurements", Jan. 2010.

Maxim Integrated Products, Inc., "Ultra-Low-Power, Single-Channel Integrated Biopotential (ECG, R-to-R, and Pace Detection) and Bioimpedance (BioZ) AFE", 2019.

D. Dobrev et al., "Two-electrode biopotential amplifier with current-driven inputs", Medical & Biological Engineering & Computing 2002, vol. 40, No. 1, pp. 122-127, 2002.

In-Duk Hwang et al., "Direct Interference Canceling for Two-Electrode Biopotential Amplifier", IEEE Transactions On Biomedical Engineering, vol. 55, No. 11, Nov. 2008, pp. 2620-2627, Nov. 2008.

D. Dobrev et al., "Two-electrode biopotential amplifier with current-driven inputs.", Medical & Biological Engineering & Computing 2002, vol. 40, pp. 122-127, IFMBE:2002, 2002.

In-Duk Hwang et al., "Direct interference canceling for two-electrode biopotential amplifier.", IEEE Transactions on Biomedical Engineering, vol. 55, No. 11, Nov. 2008, pp. 2620-2627, 2008 IEEE, Nov. 2008.

* cited by examiner

CIRCUIT APPLIED TO BIOPOTENTIAL ACQUISITION SYSTEM

CROSS REFERENCE TO RELATED APPLICATIONS

This application claims the priority of U.S. Provisional Application No. 62/770,868, filed on Nov. 23, 2018, which is included herein by reference in its entirety.

BACKGROUND

A conventional medical device generally uses large dry electrodes or wet electrodes to measure physiological signals such as electrocardiography (ECG) signals. The medical device generally has three electrodes, two of the electrodes are connecting to left body and right body, respectively, to obtain the biopotential signals, and the other electrode serves as a right-leg-drive (RLD) electrode to reduce the power line common mode interference (i.e. 60 Hz interference). Recently, personal biosensors such as portable/wearable medical devices become popular for providing physiological information at all time for the reference to the user. Considering the use and design of these portable medical devices, smaller dry electrodes are more appropriate, and the RLD electrode is removed. However, smaller dry electrodes means worse electrode impedance, and removing the RLD electrode will cause serious power line common mode interference.

To solve the problem of the worse electrode impedance of the above two-electrode portable medical device, two bias resistors are used to provide bias voltages to the input terminals of the circuit for receiving biopotential signals from the two electrodes, and resistance of the bias resistors are designed larger to improves signal quality of the biopotential signals. However, the bias resistors having large resistance will cause large common mode voltage swing, that is the power line common mode interference will become more serious. Therefore, the tradeoff between the signal quality and the power line common mode interference becomes a problem to a designer.

In addition, because the electrodes are impossible to be the same, the electrode mismatch of the two electrodes will convert the common mode voltage into differential mode voltage, and the measured biopotential signals will be influenced by this differential mode voltage caused by the electrode mismatch.

SUMMARY

It is therefore an objective of the present invention to provide a circuit applied to a biopotential acquisition system, which can effectively improve the signal quality and lower the power line common mode interference, to solve the above-mentioned problems.

According to one embodiment of the present invention, a circuit applied to a biopotential acquisition system is provided, wherein the circuit includes an active current source and an amplifier. In the operations of the circuit, the active current source is configured to provide a current to two input terminals of the circuit, wherein the two input terminals of the circuit are coupled to two input electrodes of the biopotential acquisition system; and the amplifier is configured to receive input signals from the two input terminals to generate an output signal.

According to one embodiment of the present invention, a circuit applied to a biopotential acquisition system is provided, wherein the circuit includes an amplifier and an electrode mismatch compensation circuit. In the operations of the circuit, the amplifier is configured to receive input signals from two input electrodes of the biopotential acquisition system to generate an output signal, and the electrode mismatch compensation circuit is configured to adjust the output signal to generate an adjusted output signal according to a power line frequency component of the output signal.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular system components. As one skilled in the art will appreciate, manufacturers may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". The terms "couple" and "couples" are intended to mean either an indirect or a direct electrical connection. Thus, if a first device couples to a second device, that connection may be through a direct electrical connection, or through an indirect electrical connection via other devices and connections.

Figure 1:
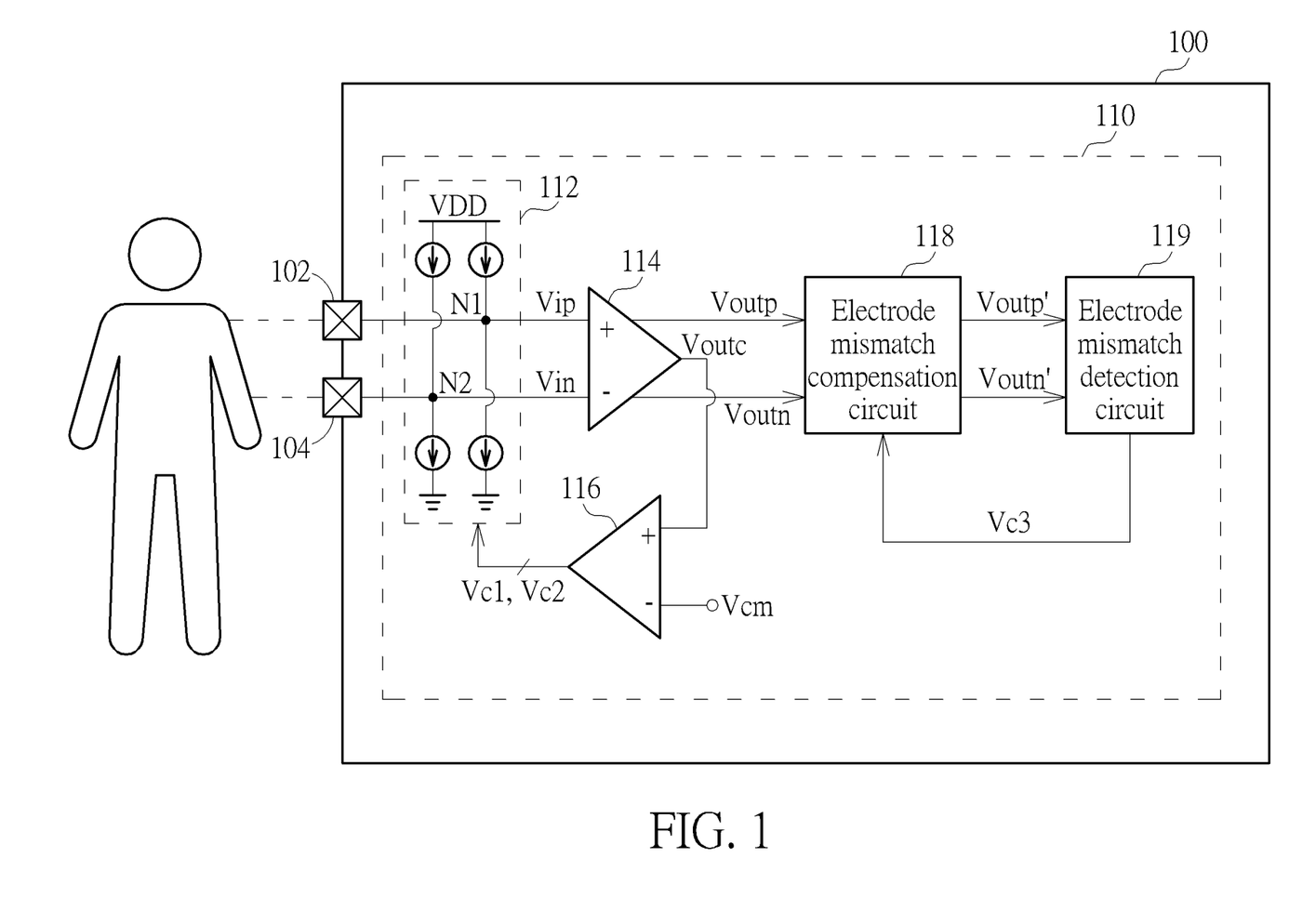
FIG. 1 is a diagram illustrating a biopotential acquisition system according to one embodiment of the present invention.

FIG. 1 is a diagram illustrating a biopotential acquisition system 100 according to one embodiment of the present invention. As shown in FIG. 1, the biopotential acquisition system 100 is a two-electrode biopotential acquisition system having only two electrodes 102 and 104, and the electrodes 102 and 104 are used to connect to a right body (e.g. right hand) and a left body (e.g. left hand) to obtain biopotential signals of a human body, and the biopotential acquisition system 100 can process and analyze the biopotential signals to determine physiological signals such as electrocardiography (ECG) signals, and the physiological features can be displayed on a screen of the biopotential acquisition system 100. In this embodiment, the biopotential acquisition system 100 can be built in any portable electronic device or a wearable electronic device.

Because the biopotential acquisition system 100 has only two electrodes 102 and 104, and no RLD electrode is used to attenuate the power line common mode interference (i.e. 60 Hz interference), a circuit 110 for processing the biopotential signals received from the electrodes 102 and 104 may suffer the serious power line common mode interference. In order to obtain the signals with higher quality and reduce the impact of the power line common mode interference, the circuit 110 within the biopotential acquisition system 100 is designed to have high differential input impedance and low common mode input impedance to achieve the desired effect. In detail, the circuit 110 has two input terminals N1 and N2, an active current source 112, an amplifier 114, a feedback circuit 116, an electrode mismatch compensation circuit 118 and an electrode mismatch compensation circuit 119. In the operations of the circuit 110, the two input terminals N1 and N2 are connected to the electrodes 102 and 104, respectively, and receive input signals (i.e. biopotential signals) Vip and Vin from the electrodes 102 and 104. The active current source 112 is used to provide currents to the input terminals N1 and N2, and the amplifier 114 receives the input signals Vip and Vin from the two input terminals N1 and N2 to generate differential output signal Voutp and Voutn. Then, the feedback circuit 116, which can be implemented by a transconductance amplifier, compares a common mode signal Voutc of the differential output signal Voutp and Voutn with a reference common mode voltage Vcm to generate control signals Vc1 and Vc2 to control the active current source 112. In this embodiment, by setting the active current source 112 before the amplifier 114, the active current source 112 can be regarded as a resistor with large resistance for the differential signals (i.e. input signals Vip and Vin), so the input signals Vip and Vin will have better signal quality that is appropriate for the following operations. Specifically, if the electrodes 102 and 104 of the biopotential acquisition system 100 are small dry electrodes, the electrodes 102 and 104 will have large impedance, so the active current source 112 having high resistance for the differential signals can reduce voltage drop to increase the signal quality. In addition, by setting the feedback circuit 116, if the human body suffers the power line common mode interference, the common mode signal Voutc outputted by amplifier 114 will include this power line common mode interference, and the feedback circuit 116 can immediately adjust the current provided by the active current source 112 to attenuate the impact of the power line common mode interference. By setting the feedback circuit 116, the active current source 112 and the feedback circuit 116 can be regarded as a resistor with small resistance for the common mode signal, so the power line common mode interference will be greatly reduced, that is the biopotential acquisition system 100 has higher common mode signal swing tolerance.

Figure 2:
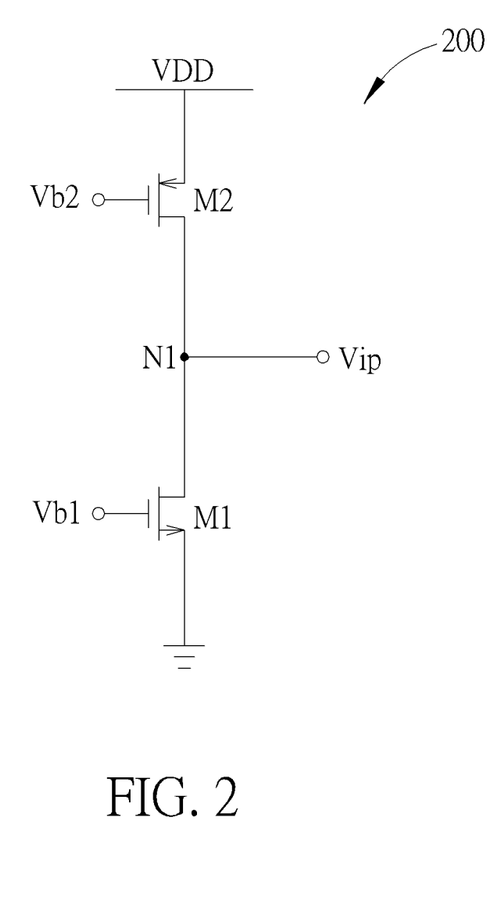
FIG. 2 is a diagram illustrating a current source according to a first embodiment of the present invention

FIG. 2 is a diagram illustrating a current source 200 according to a first embodiment of the present invention, wherein the current source 200 is used to implement a portion of the active current source 112 shown in FIG. 1. As shown in FIG. 2, the current source 200 comprises an N-type transistor M1 and a P-type transistor M2 coupled between a supply voltage VDD and a ground voltage, the N-type transistor M1 and the P-type transistor M2 are controlled by voltages Vb1 and Vb2, respectively, and the drain electrode of the N-type transistor M1 is connected to the input terminal N1. In this embodiment, the voltages Vb1 and Vb2 are determined according to the control signals Vc1 and Vc2 generated by the feedback circuit 116, or the control signals Vc1 and Vc2 can serve as the voltages Vb1 and Vb2. The current source 200 shown in FIG. 2 is used to provide the current to the input terminal N1, and another current source having the similar structure can be used to provide the current to the input terminal N2.

Figure 3:
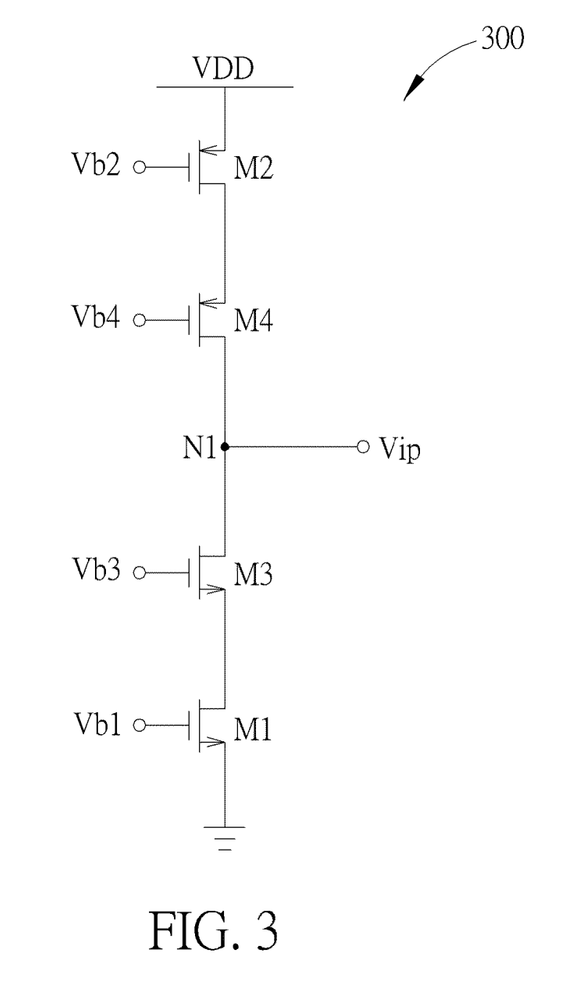
FIG. 3 is a diagram illustrating a current source according to a second embodiment of the present invention

FIG. 3 is a diagram illustrating a current source 300 according to a second embodiment of the present invention, wherein the current source 300 is used to implement a portion of the active current source 112 shown in FIG. 1. As shown in FIG. 3, the current source 300 comprises two N-type transistors M1 and M3 and two P-type transistors M2 and M4 coupled between the supply voltage VDD and a ground voltage, the N-type transistor M1, the P-type transistor M2, the N-type transistor M3, the P-type transistor M4 are controlled by voltages Vb1, Vb2, Vb3 and Vb4, respectively, and the drain electrode of the N-type transistor M3 is connected to the input terminal N1. In this embodiment, the voltages Vb1 and Vb2 are determined according to the control signals Vc1 and Vc2 generated by the feedback circuit 116, or the control signals Vc1 and Vc2 can serve as the voltages Vb1 and Vb2. The current source 300 shown in FIG. 3 is used to provide the current to the input terminal N1, and another current source having the similar structure can be used to provide the current to the input terminal N2. The current source 300 having cascode structure has higher differential input impedance than the current source 200 shown in FIG. 2.

Figure 4:
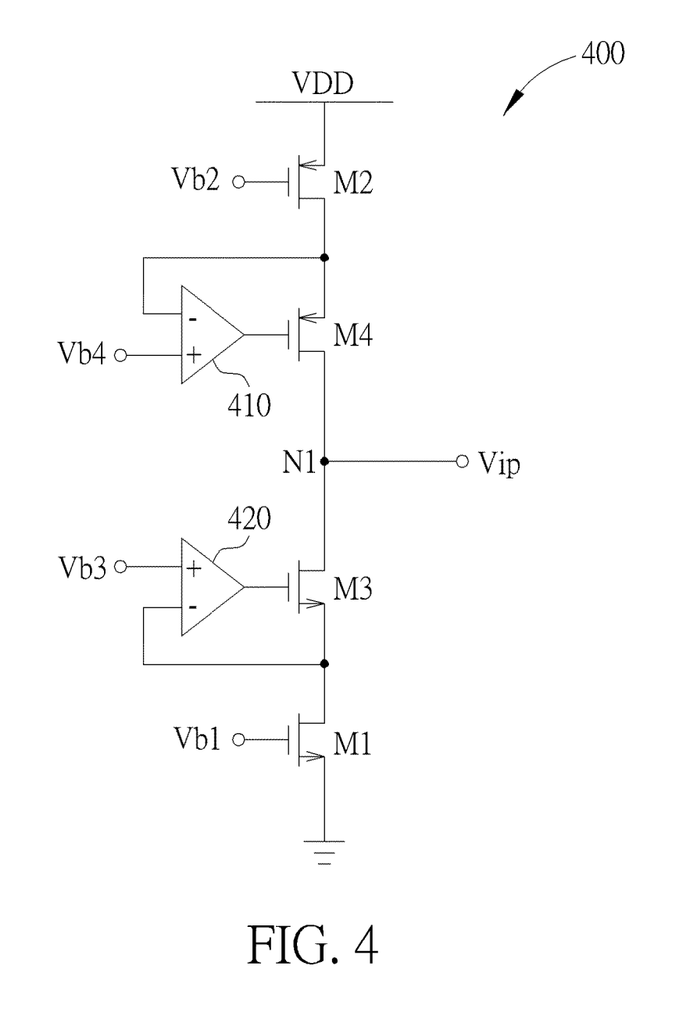
FIG. 4 is a diagram illustrating a current source according to a third embodiment of the present invention

FIG. 4 is a diagram illustrating a current source 400 according to a third embodiment of the present invention, wherein the current source 400 is used to implement a portion of the active current source 112 shown in FIG. 1. As shown in FIG. 3, the current source 400 comprises two N-type transistors M1 and M3 and two P-type transistors M2 and M4 coupled between the supply voltage VDD and a ground voltage, and two operational amplifiers 410 and 420. The N-type transistor M1 and the P-type transistor M2 are controlled by the voltages Vb1 and Vb2, respectively, and the N-type transistor M3 and the P-type transistor M4 are controlled by output signals of the operational amplifiers 420 and 410, respectively, wherein a negative input terminal of the operational amplifier 410 is coupled to a source electrode of the P-type transistor M4, a positive input terminal of the operational amplifier 410 is connected to a voltage Vb4, a negative input terminal of the operational amplifier 420 is coupled to a source electrode of the N-type transistor M3, a positive input terminal of the operational amplifier 420 is connected to a voltage Vb3. In this embodiment, the voltages Vb1 and Vb2 are determined according to the control signals Vc1 and Vc2 generated by the feedback circuit 116, or the control signals Vc1 and Vc2 can serve as the voltages Vb1 and Vb2. The current source 400 shown in FIG. 4 is used to provide the current to the input terminal N1, and another current source having the similar structure can be used to provide the current to the input terminal N2. The current source 400 has higher differential input impedance than the current source 300 shown in FIG. 3.

Figure 5:
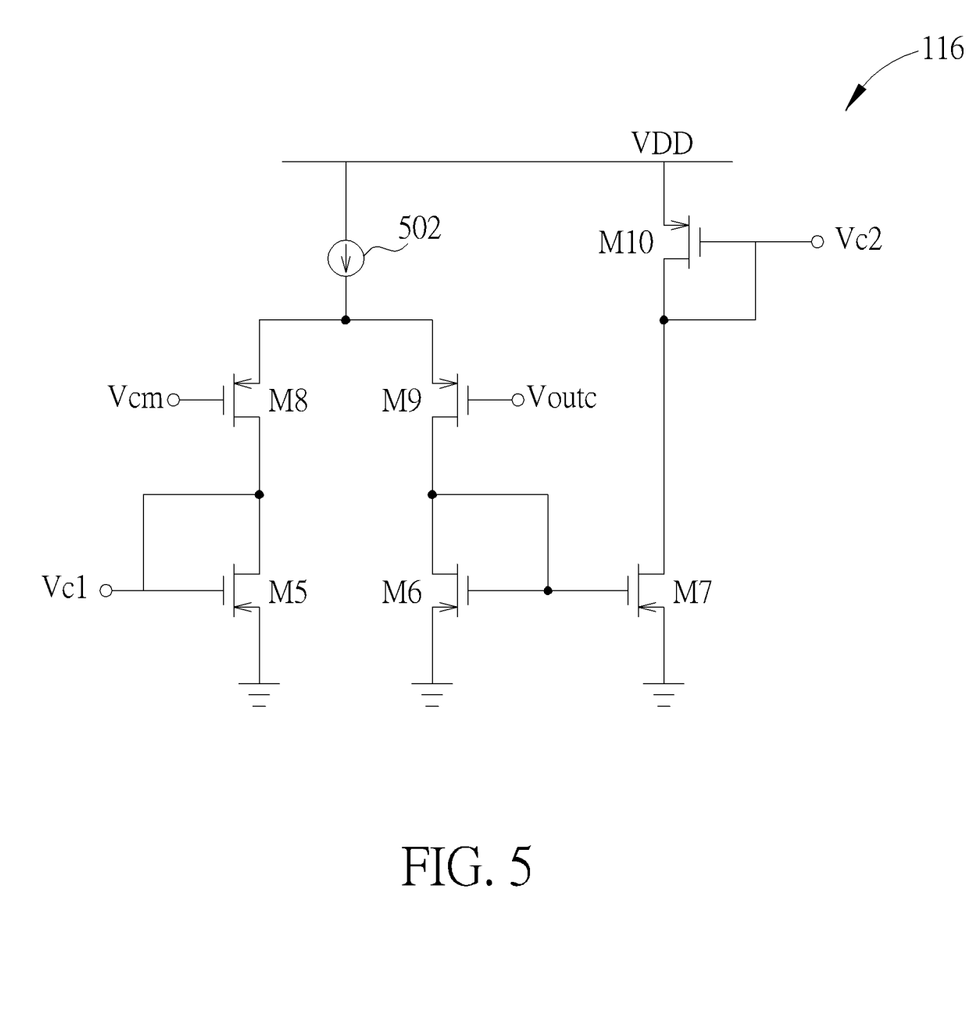
FIG. 5 is a diagram illustrating the feedback circuit according to one embodiment of the present invention.

FIG. 5 is a diagram illustrating the feedback circuit 116 according to one embodiment of the present invention. As shown in FIG. 5, the feedback circuit 116 is implemented by the current mirror transconductance amplifier comprising a current source 502, three N-type transistors M5, M6 and M7 and three P-type transistors M8, M9 and M10. In FIG. 5, gate electrodes of the P-type transistors M8 and M9 receive the reference common mode voltage Vcm and the common mode signal Voutc, respectively, and voltages at a gate electrode of the N-type transistor M5 and a gate electrode of the P-type transistor M10 serve as the control signals Vc1 and Vc2, respectively. In this embodiment, the control signals Vc1 and Vc2 can serve as the voltage Vb1 and Vb2 shown in FIGS. 2-4, respectively.

In another embodiment, the current source 502 shown in FIG. 5 can be replaced by an adaptive current source to reduce the current source noise.

In addition, because the mismatch between the electrodes 102 and 104 will convert the common mode voltage into differential mode voltage, and the input signals Vip and Vin may be influenced by this differential mode voltage. In order to cancel this differential mode voltage in the interference band, the electrode mismatch compensation circuit 118 and the electrode mismatch detection circuit 119 are designed in the circuit 110. In the operations of the electrode mismatch compensation circuit 118 and the electrode mismatch detection circuit 119, the electrode mismatch compensation circuit 118 is configured to adjust the differential output signal Voutp and Voutn to generate an adjusted differential output signal Voutp' and Voutn' according to a compensation signal Vc3, wherein the compensation signal Vc3 indicates a power line frequency component of the adjusted differential output signal. The electrode mismatch detection circuit 119 is configured to detect the power line frequency component of the adjusted differential output signal Voutp' and Voutn' to generate the compensation signal Vc3.

Figure 6:
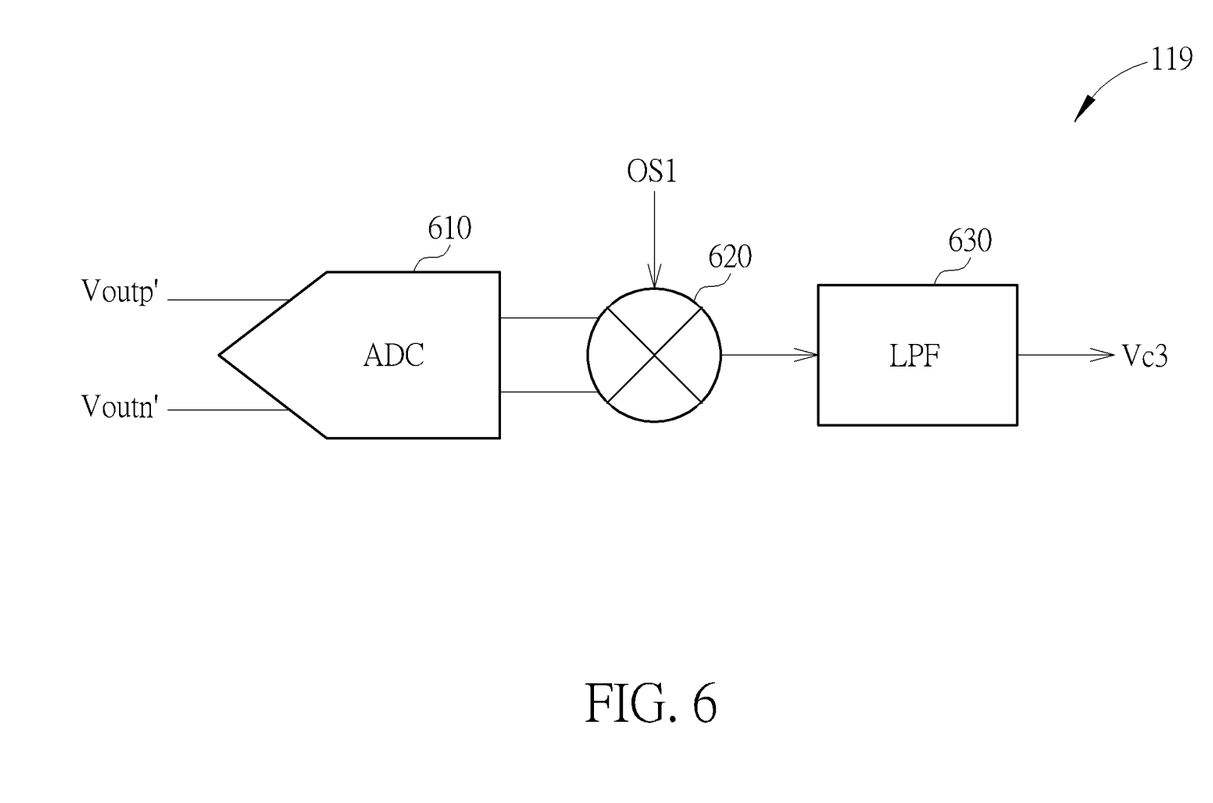
FIG. 6 is a diagram illustrating the electrode mismatch detection circuit according to one embodiment of the present invention.

FIG. 6 is a diagram illustrating the electrode mismatch detection circuit 119 according to one embodiment of the present invention. As shown in FIG. 6, the electrode mismatch detection circuit 119 comprises an analog-to-digital converter (ADC) 610, a mixer 620 and a low-pass filter (LPF) 630. In the operations of the electrode mismatch detection circuit 119, the ADC 610 performs an analog-to-digital operations upon the adjusted differential output signal Voutp' and Voutn' to generate a digital adjusted differential output signal, and the mixer 620 mixes the digital adjusted differential output signal with an oscillation signal OS1 to generate a mixed signal, wherein a frequency the oscillation signal OS1 is equal to a power line frequency such as 60 Hz. Then, the LPF 630 filters the mixed signal to generate the compensation signal Vc3. In this embodiment, the compensation signal Vc3 represents the strength of the power line frequency component.

Figure 7:
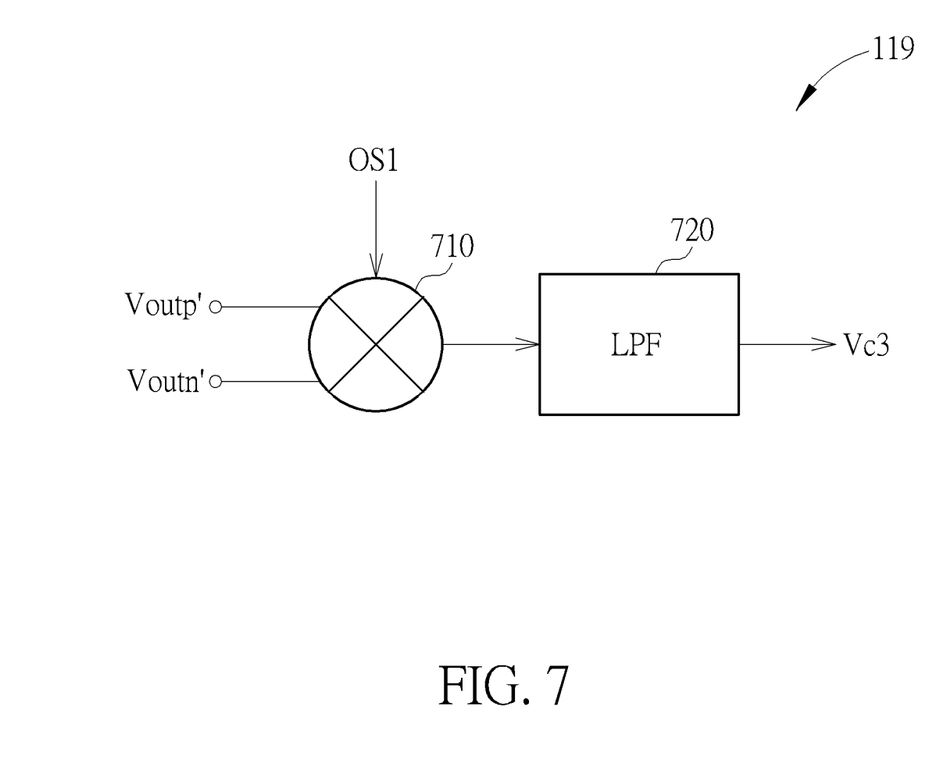
FIG. 7 is a diagram illustrating the electrode mismatch detection circuit according to another embodiment of the present invention.

FIG. 7 is a diagram illustrating the electrode mismatch detection circuit 119 according to another embodiment of the present invention. As shown in FIG. 7, the electrode mismatch detection circuit 119 comprises a mixer 710 and a LPF 720. In the operations of the electrode mismatch detection circuit 119, the mixer 710 mixes the adjusted differential output signal Voutp' and Voutn' with an oscillation OS1 to generate a mixed signal, wherein a frequency the oscillation OS1 is equal to a power line frequency such as 60 Hz. Then, the LPF 720 filters the mixed signal to generate the compensation signal Vc3. In this embodiment, the compensation signal Vc3 represents the strength of the power line frequency component.

Figure 8:
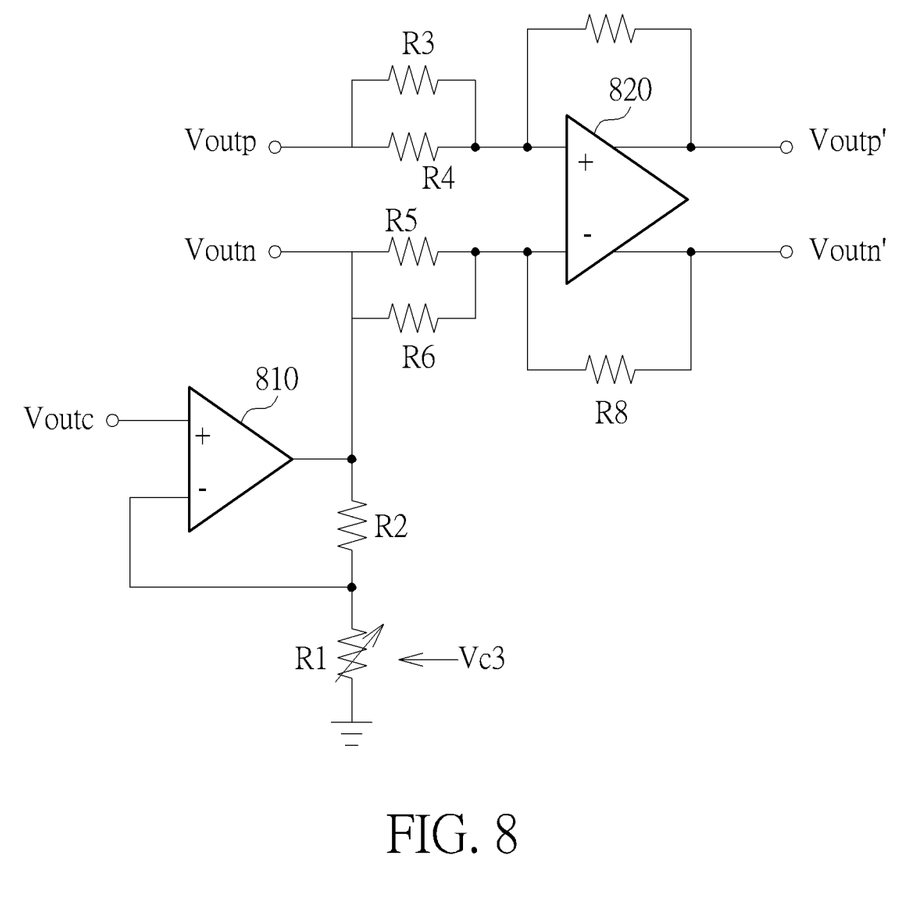
FIG. 8 is a diagram illustrating the electrode mismatch compensation circuit according to one embodiment of the present invention.

FIG. 8 is a diagram illustrating the electrode mismatch compensation circuit 118 according to one embodiment of the present invention. As shown in FIG. 8, the electrode mismatch compensation circuit 118 comprises two operational amplifiers 810 and 820, and a variable resistor R1 and a plurality of resistors R2-R8, wherein a resistance of the variable resistor R1 is controlled by the compensation signal Vc3. In the embodiment shown in FIG. 8, the operational amplifier 810 and the variable resistor R1 serves as an analog variable gain single to differential amplifier, and the operational amplifier 820 serves as an analog to digital summing amplifier for summing the differential output signal Voutp and Voupn and the outputs of the operational amplifier 820 to generate the adjusted differential output signal Voutp' and Voutn'.

Figure 9:
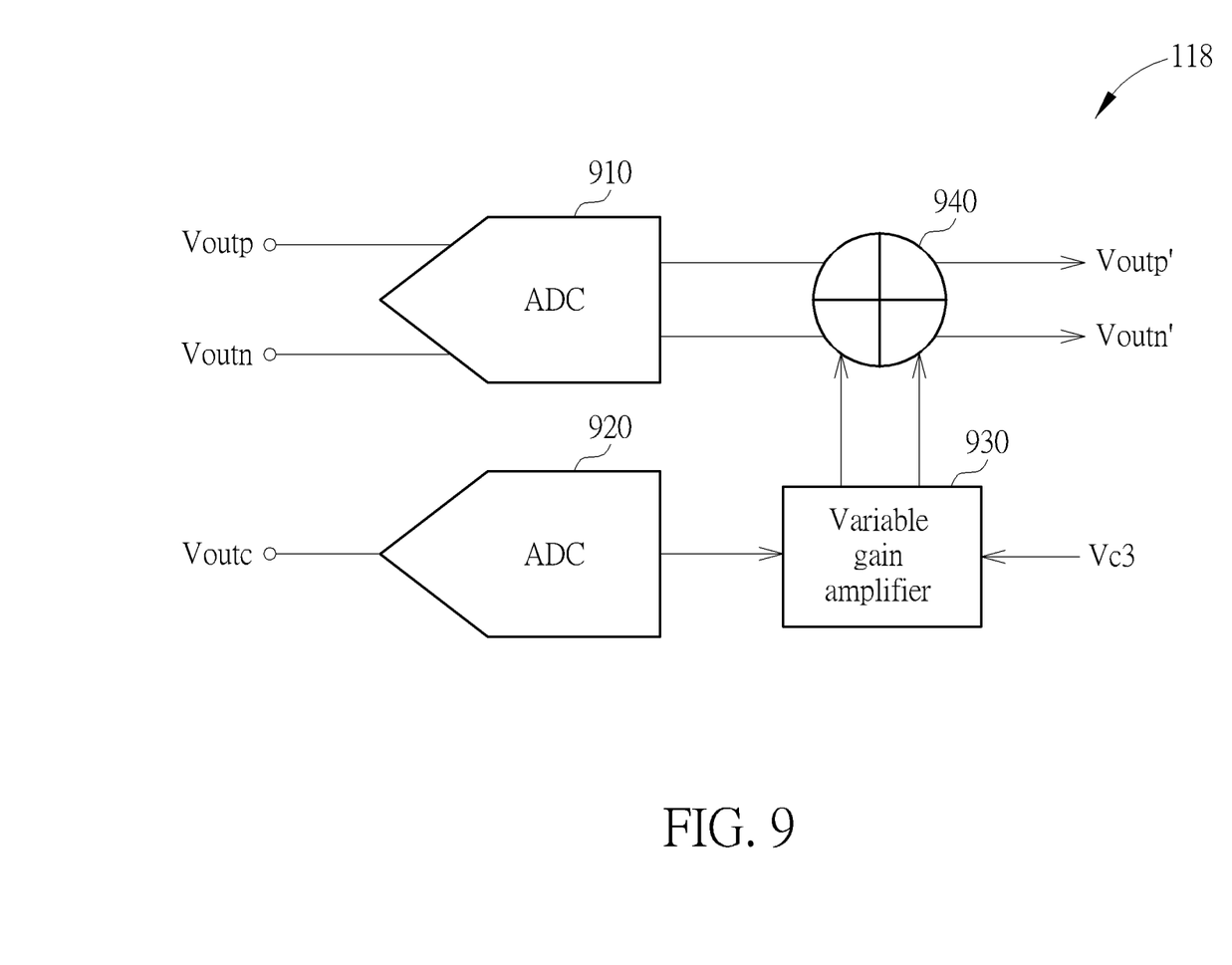
FIG. 9 is a diagram illustrating the electrode mismatch compensation circuit according to another embodiment of the present invention.

FIG. 9 is a diagram illustrating the electrode mismatch compensation circuit 118 according to another embodiment of the present invention. As shown in FIG. 9, the electrode mismatch compensation circuit 118 comprises two ADCs 910 and 920, a variable gain amplifier 930 and a combiner 940. In the operations of the electrode mismatch compensation circuit 118, the ADC 910 performs the analog-to-digital converting operations upon the differential output signal Voutp and Voutn to generate a digital differential output signal, the ADC 920 performs the analog-to-digital converting operations upon the common mode signal Voutc to generate a digital common mode signal, the variable gain amplifier 930 refers to the compensation signal Vc3 to convert the digital common mode signal into a differential signal, and the combiner 940 combines the digital differential output signal with the differential signal outputted by the variable gain amplifier 930 to generate the adjusted differential output signal Voutp' and Voutn'.

Briefly summarized, in the circuit applied to the biopotential acquisition system of the present invention, the active current source coupled to the input terminals and related feedback circuit are designed to provide high differential input impedance and low common mode impedance to improve signal quality and reduce the power line common mode interference simultaneously. In addition, the electrode mismatch compensation circuit and the electrode mismatch detection circuit are designed to reduce the differential mode voltage in the interference band caused by the electrode mismatch, to improve the accuracy of the biopotential signals.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A circuit applied to a biopotential acquisition system, comprising:
an active current source, for providing a current to two input terminals of the circuit, wherein the two input terminals of the circuit are coupled to two input electrodes of the biopotential acquisition system;
an amplifier, for receiving input signals from the two input terminals to generate two output signals, wherein the two output signals form a differential output signal; and
a feedback circuit, for generating a control signal to control the active current source according to the two output signals;
wherein the active current source comprises a first current source and a second current source, the first current source is coupled between one of the two input terminals and a supply voltage, the second current source is coupled between the one of the two input terminals and a ground voltage, and the first current source and the second current source are controlled according to the control voltage.

2. The circuit of claim 1, wherein the feedback circuit receives a common mode signal of the differential output signal to generate the control signal to control the active current source.

3. The circuit of claim 1, wherein the feedback circuit is a transconductance amplifier.

4. The circuit of claim 2, wherein the transconductance amplifier comprises another active current source to reduce current source noise.

5. The circuit of claim 1, wherein the biopotential acquisition system is a two-electrode biopotential acquisition system.

6. The circuit of claim 1, further comprising:
an electrode mismatch compensation circuit, coupled to the amplifier, for adjusting the two output signals to generate two adjusted output signals according to a power line frequency component of the two output signals.

7. The circuit of claim 6, further comprising:
an electrode mismatch detection circuit, for detecting the power line frequency component of the two adjusted output signals to generate a compensation signal to the electrode mismatch compensation circuit to adjust the two output signals.

8. The circuit of claim 7, wherein the electrode mismatch detection circuit comprises:
a mixer, for mixing the two adjusted output signals with oscillation signals to generate mixed signals, wherein a frequency the oscillation signals is equal to a power line frequency; and
a low-pass filter, coupled to the mixer, for receiving the mixed signals to generate the compensation signal.

9. The circuit of claim 7, wherein the electrode mismatch detection circuit comprises:
an ADC, configured to perform an analog-to-digital converting operation upon the two adjusted output signals to generate two digital adjusted output signals;
a mixer, for mixing the two digital adjusted output signals with oscillation signals to generate mixed signals, wherein a frequency the oscillation signals is equal to a power line frequency; and
a low-pass filter, coupled to the mixer, for receiving the mixed signals to generate the compensation signal.

10. The circuit of claim 6, wherein the electrode mismatch compensation circuit comprises:
a first ADC, configured to perform an analog-to-digital converting operation upon the two output signals to generate a digital differential output signal;
a second ADC, configured to perform the analog-to-digital converting operation upon a common mode signal of the two output signals to generate a digital common mode signal;
wherein the digital differential output signal is adjusted to generate the two adjusted output signal according to the digital common mode signal and the power line frequency component of the two output signals.

11. The circuit of claim 10, wherein the electrode mismatch compensation circuit further comprises:
a variable gain amplifier, configured to refer to the power line frequency component to convert the digital common mode signal into a differential signal; and
a combiner, coupled to the first ADC and the variable gain amplifier, configured to combine the digital differential output signal with the differential signal to generate the two adjusted output signal.

12. The circuit of claim 1, wherein the two input terminals comprise a first input terminal and a second input terminal, the one of the two input terminals is the first input terminal; and the active current source further comprises a third current source and a fourth current source, the third current source is coupled between the second input terminal and the supply voltage, the fourth current source is coupled between the second input terminal and the ground voltage, and the third current source and the fourth current source are controlled according to the control voltage.

13. A circuit applied to a biopotential acquisition system, comprising:
an amplifier, for receiving input signals from two input electrodes of the biopotential acquisition system to generate two output signals, wherein the two output signal form a differential output signal;
an electrode mismatch compensation circuit, coupled to the amplifier, for adjusting the two output signal to generate two adjusted output signal according to a power line frequency component of the two output signals;
wherein the electrode mismatch compensation circuit comprises:
a first analog-to-digital converter (ADC), configured to perform an analog-to-digital converting operation upon the two output signals to generate a digital differential output signal;
a second ADC, configured to perform the analog-to-digital converting operation upon a common mode signal of the two output signals to generate a digital common mode signal;
wherein the digital differential output signal is adjusted to generate the two adjusted output signal according to the digital common mode signal and the power line frequency component of the two output signals.

14. The circuit of claim 13, further comprising:
an electrode mismatch detection circuit, for detecting the power line frequency component of the two adjusted output signals to generate a compensation signal to the electrode mismatch compensation circuit to adjust the two output signals.

15. The circuit of claim 14, wherein the electrode mismatch detection circuit comprises:
a mixer, for mixing the two adjusted output signals with oscillation signals to generate mixed signals, wherein a frequency the oscillation signals is equal to a power line frequency; and
a low-pass filter, coupled to the mixer, for receiving the mixed signals to generate the compensation signal.

16. The circuit of claim 14, wherein the electrode mismatch detection circuit comprises:
an ADC, configured to perform an analog-to-digital converting operation upon the two adjusted output signals to generate two digital adjusted output signals;
a mixer, for mixing the two digital adjusted output signals with oscillation signals to generate mixed signals, wherein a frequency the oscillation signals is equal to a power line frequency; and
a low-pass filter, coupled to the mixer, for receiving the mixed signals to generate the compensation signal.

17. The circuit of claim 13, wherein the biopotential acquisition system is a two-electrode biopotential acquisition system.

18. The circuit of claim 13, wherein the electrode mismatch compensation circuit further comprises:
a variable gain amplifier, configured to refer to the power line frequency component to convert the digital common mode signal into a differential signal; and
a combiner, coupled to the first ADC and the variable gain amplifier, configured to combine the digital differential output signal with the differential signal to generate the two adjusted output signal.

\* \* \* \* \*